United States Patent [19]
Wong

[11] Patent Number: 5,502,308
[45] Date of Patent: *Mar. 26, 1996

[54] DIFFUSION-TYPE GAS SAMPLE CHAMBER

[75] Inventor: Jacob Y. Wong, Santa Barbara, Calif.

[73] Assignee: Gaztech International Corporation, Goleta, Calif.

[*] Notice: The term of this patent shall not extend beyond the expiration date of Pat. No. 5,163,332.

[21] Appl. No.: 279,915

[22] Filed: Jul. 25, 1994

Related U.S. Application Data

[63] Continuation-in-part of Ser. No. 915,003, Jul. 16, 1992, Pat. No. 5,340,986.

[51] Int. Cl.$^6$ .................................................. G01N 21/61
[52] U.S. Cl. ............................ 250/338.5; 250/343
[58] Field of Search ......................... 250/343, 338.5; 356/437

[56] References Cited

U.S. PATENT DOCUMENTS 3,834,123  9/1974  Margraf ...................................... 55/430
3,968,367  7/1976  Berg ......................................... 250/343
4,749,276  6/1988  Bragg et al. ............................. 250/343
5,163,332  11/1992  Wong ...................................... 250/343

Primary Examiner—Carolyn E. Fields
Attorney, Agent, or Firm—Daniel C. McKown

[57] ABSTRACT

Apparatus for measuring the concentration of a gas present in a sample chamber by ambient pressure diffusion employs a nondispersive infrared gas analysis technique. The sample chamber has the form of a tube that is closed at one end, with a source of radiation and a detector mounted side by side at the other end. The inwardly-facing surfaces of the tube are specularly reflective, whereby the optical length of the sample chamber is twice its physical length. A gas filter cell located in the optical path permits the concentration of an analyte gas to be measured accurately despite the presence in the sample chamber of an interfering gas. A small ultrasonic vibrator affixed to the wall of the sample chamber prevents unwanted particles from accumulating on the semi-permeable membranes through which ambient gases diffuse into and out of the sample chamber.

9 Claims, 2 Drawing Sheets

DIFFUSION-TYPE GAS SAMPLE CHAMBER

RELATED APPLICATIONS

The present application is a continuation-in-part of U.S. applications Ser. No. 07/915,003 for DIFFUSION-TYPE GAS SAMPLE CHAMBER filed Jul. 16, 1992, now U.S. Pat. No. 5,340,986. The disclosure of that application is incorporated herein by reference to avoid unnecessary repetition of background material.

FIELD OF THE INVENTION

The present invention is in the field of gas analysis, and specifically relates to apparatus using a nondispersive infrared gas analysis technique to determine the concentration of a particular type of gas present in a sample chamber by sensing the absorption of infrared radiation passing through the gas.

THE PRIOR ART

A comparatively new development in the field of nondispersive infrared gas analyzers has been the diffusion-type gas sample chamber. In a diffusion-type gas sample chamber, the gas to be measured enters and leaves the chamber by diffusion.

One example of a diffusion-type gas sample chamber is described in the parent application. In that invention, the sample chamber has the form of a tube composed of a gastight material, having apertures covered by semipermeable membranes through which the gas to be measured enters and leaves the sample chamber by diffusion. This same approach is used in the present invention, with some important modifications.

Another example of a diffusion-type gas sample chamber is described in U.S. Pat. No. 4,709,150 to Burough et al. In their invention, the body of the sample chamber is composed of a porous material through which the gas to be measured passes by diffusion. Burough et al. do not teach or suggest using the walls of the porous tube as reflective radiation-guiding elements.

An example of a non-diffusion-type gas sample chamber is shown in Japanese Patent Publication No. 59-173734(A) of Miyazaki. In that analyzer, the sample cells have the form of helical tubes. The gas to be measured must be pressurized to force it to flow through the sample tube.

Another example of a non-diffusion-type of gas sample chamber is shown in Japanese Publication No. 63-298031 by Fujimura, in which air is rammed into the sample chamber by motion of the sample chamber through the air.

In the present application, the inventor will describe improvements on the sample chamber described in the parent application, to improve its performance.

In keeping with chemical practice, the gas to be analyzed is called the analyte gas. In the sensor of the parent application, the concentration of the analyte gas is related to the absorption of radiation by a gas sample containing the analyte gas. A steady amount of radiation is passed through the gas sample chamber. Ideally, the wavelength of the radiation coincides with the wavelength of an absorption band of the analyte gas, so that a reduction in the received radiation signals the presence of the analyte gas, and the amount of the reduction is related to the concentration of the analyte gas.

In practically all applications, the analyte gas is not the only gas present in the sample chamber. Typically, one might want to measure the concentration of carbon dioxide in air or the concentration of carbon monoxide in exhaust gas.

Depending on the gases present and on the wavelength of the radiation used, it can happen that an absorption band of one of the other gases present may partially overlap the chosen absorption band of the analyte gas. When this situation obtains, it is impossible for the detector to distinguish absorption caused by the analyte gas from absorption caused by the other gas, which is called the interfering gas. In the following description, the present inventor will disclose apparatus for solving this problem, thereby permitting reliable measurement of the concentration of the analyte gas despite the presence of an interfering gas.

A second improvement described below arose from a different type of problem that could occur to the sensor of the parent application. In that sensor, ambient gas enters and leaves the gas sample chamber through apertures in the wall of the chamber that are covered by a semipermeable membrane. If the semipermeable membranes were not used, there would be a tendency for particles of dust or smoke or microscope droplets of water or oil to enter the sample chamber and deposit themselves on the optical surfaces, thereby impairing the performance of the surfaces and conceivably providing interfering absorption bands. The purpose of the semipermeable membranes covering the apertures is to keep such unwanted particles and droplets out of the sample chamber, but without interfering with the desired diffusion of gases into and out of the sample chamber.

In a dirty environment, where heavy concentrations of contaminant particles and droplets are encountered, it is possible for the semipermeable membranes to work so well that the membranes become clogged with the contaminants. This could impede the diffusion of gas through the semipermeable membrane. In the description below the inventor will disclose a solution for this problem.

SUMMARY OF THE INVENTION

The problem of an interfering gas in the gas sample chamber is solved in accordance with the present invention by inserting a gas filter cell into the gas sample chamber. Since the radiation emitted by the source at one end of the chamber is reflected from the other end of the chamber back to the first end, the radiation passes twice through the gas filter cell.

The gas filter cell is filled with the interfering gas, which may even be pressurized to increase its concentration. In passing twice through the gas filter cell, the radiation generated by the source is greatly attenuated at wavelengths corresponding to the absorption bands of the interfering gas. Since interference occurs only at wavelengths where the absorption bands of the interfering gas overlap the absorption bands of the analyte gas, the great attenuation of the radiation of such wavelengths by the gas filter cell substantially eliminates the possibility of interference.

Although gas filter cells have long been used for unidirectional filtering of a beam of radiation, no reference has been found to their use in a bidirectional mode. The bidirectional mode is especially attractive in the gas sample chamber of the present invention because it conserves space, the radiation pathlength being twice the physical length of the cell.

In the present invention the gas filter cell is far superior to any conventional interference filter because the absorption spectrum of the gas filter cell necessarily is identical to the absorption spectrum of the interfering gas.

The problem of dust particles and/or droplets clogging the semipermeable membranes was solved by affixing small low-powered ultrasonic vibrators to the body of the gas sample chamber adjacent the apertures through which the gases enter and leave the chamber. The vibrations are transmitted to the semipermeable membranes through the wall of the gas sample chamber. As the semipermeable membrane vibrates at a microscopic amplitude, portions of it collide with the unwanted particles and droplets knocking them away from the semipermeable membrane.

The novel features which are believed to be characteristic of the invention, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

DETAILED DESCRIPTION OF THE PREFERRED EMBODIMENT

Figure 1:
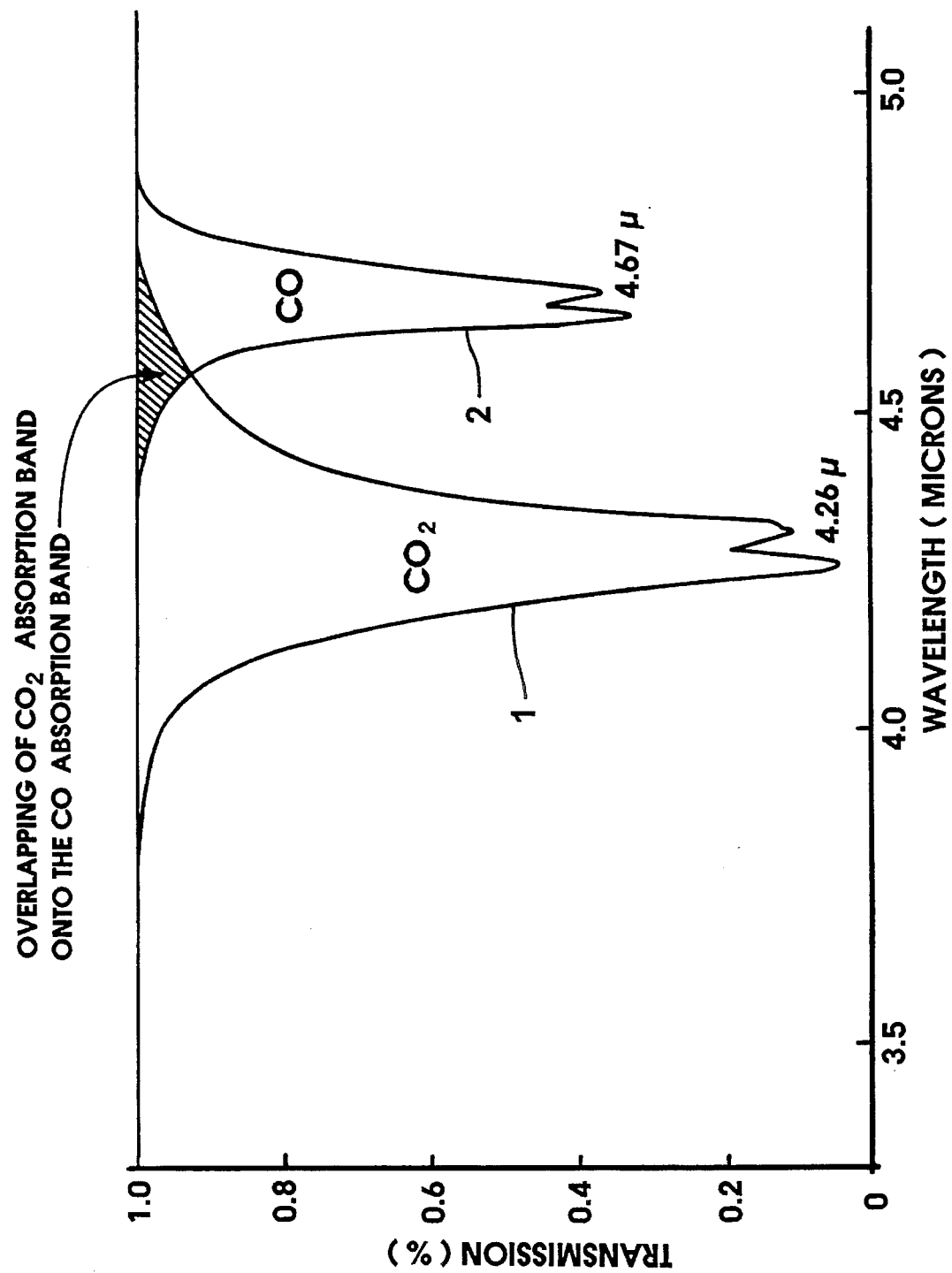
FIG. 1 is a graph showing the absorption spectra of carbon dioxide and of carbon monoxide/in the infrared portion of the spectrum.

FIG. 1 shows an absorption band 1 of carbon dioxide and an absorption band 2 of carbon monoxide. In keeping with the usual practice in the art, the graphs of FIG. 1 show transmission through standard gas samples as a function of wavelength, so that the absorption bands will appear as dips in the graphs. FIG. 1 does not show the absorption spectrum of a mixture of the two gases.

As indicated by the hatched area of FIG. 1, the two absorption bands overlap in the vicinity of 4.55 microns.

If one were attempting to measure the concentration of carbon monoxide, it would be called the analyte gas. If the gas sample included some carbon dioxide, in addition to the carbon monoxide and some non-absorbing gases, then the absorption measured at 4.55 microns would be too large owing to the absorption by the carbon dioxide, leading one to think the concentration of carbon monoxide is greater than it really is. This type of error is referred to as interference, and the carbon dioxide would be called the interfering gas. Not only is the total absorption in this case greater than it should be if only the analyte gas were present, but to make matters worse, it is not possible to determine how much of the absorption is caused by the analyte gas and how much is caused by the interfering gas.

Although interference is very detrimental to the objective of a gas analyzer, it can be used to advantage in other instruments, as described by the present inventor in U.S. Pat. No. 5,335,534 issued Aug. 9, 1994, for "Testing Method for Toxic Gas Sensors."

The absorption spectra of all of the common gases are now well documented, and the possibility of interference can be determined by reference to a handbook, well in advance of any measurements. In most practical situations, interference is the rule rather than the exception. For example, gaseous products of combustion might be expected to include both carbon dioxide and carbon monoxide in proportions related to the completeness of the combustion. Therefore, it is highly desirable in a practical gas analysis instrument to be able to measure the concentration of the analyte gas in the presence of one or more interfering gases. How this is achieved in the present invention will now be described in relation to FIG. 2, which shows a preferred embodiment of the present invention.

Figure 2:
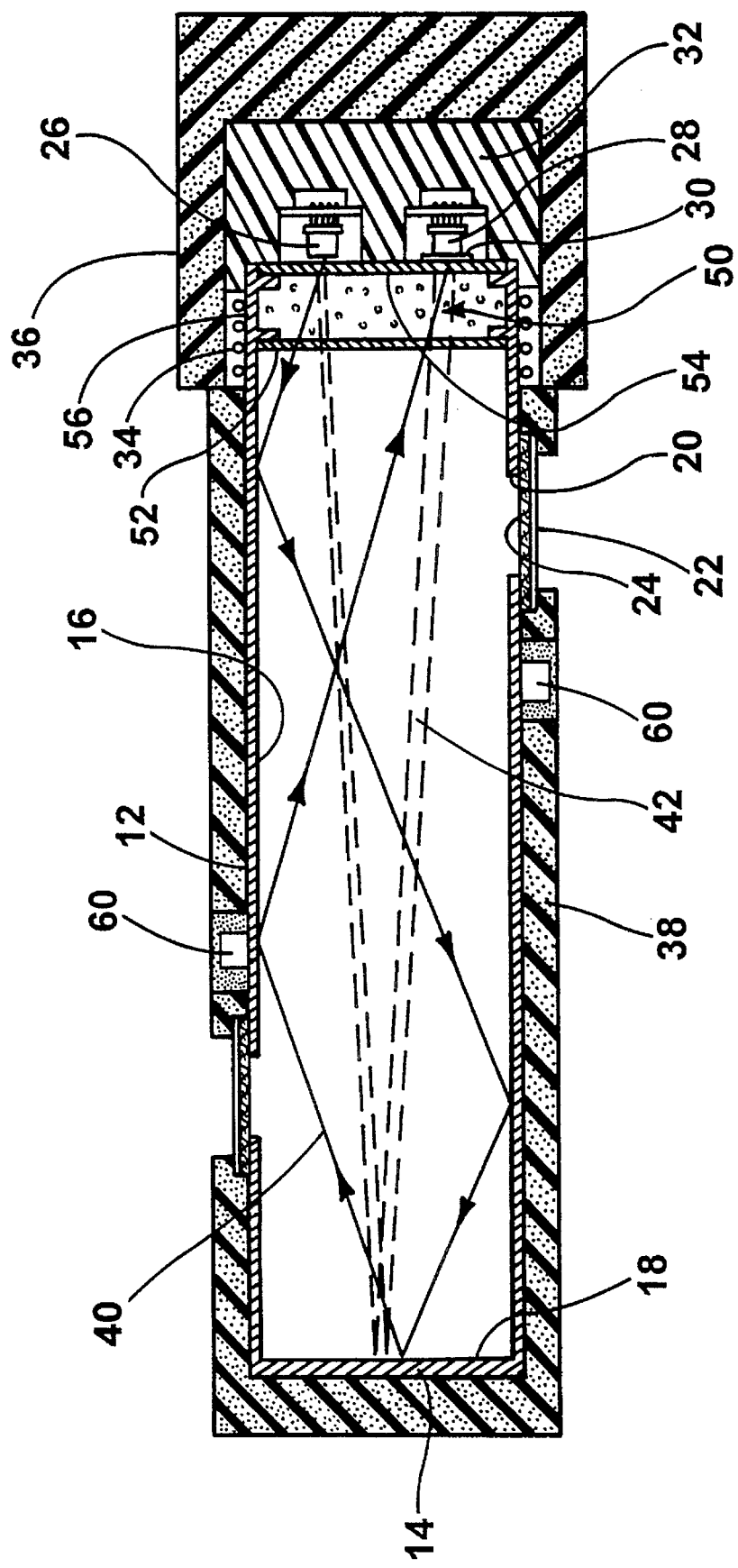
FIG. 2 is a side elevational cross-sectional view of the improved diffusion-type gas sample chamber of the present invention.

As shown in FIG. 2, the gas sample chamber of the present invention includes a tube 12 having a closed end 14 and having an open end. In the preferred embodiment, the tube 12 is composed of a metal, and has a square cross section. In other embodiments, the cross section is circular.

The surface of the inner wall 16 of the tube 12 and the inwardly-facing surface 18 of the closed end 14 are specularly-reflective.

In accordance with the present invention, the metal tube 12 is gastight and therefore filtering apertures, of which the filtering aperture 20 is typical, are provided at spaced locations along the tube 12 to permit molecules of the ambient gas to enter and to leave the space within the tube. Each of the filtering apertures 20 is covered by a sheet of a semipermeable membrane 22.

In the preferred embodiment, the analyte gas is carbon dioxide, and the semipermeable membrane is composed of silicone rubber and is approximately 25 to 50 microns thick. Because of its fragility, in the preferred embodiment the semipermeable membrane 22 is supported by a mesh 24 that spans the aperture 20. At this point in time, the exact number, location, and disposition of the filtering apertures does not appear to be crucial, although some as-yet-undiscovered arrangement may be optimal.

The open end of the tube 12 is closed by a cap 32 in which are mounted a source 26 of radiation, a detector 28, and a narrow passband filter 30. The passband of the filter 30 is located at a wavelength at which the analyte gas strongly absorbs radiation and at which any other gases that might be present do not absorb. The plastic cap 32 serves to mount the source 26 and the detector 28 and the filter 30 in the open end of the tube 12 with the source 26 and the detector 28 facing the surface 18.

Some of the radiation emitted by the source 26 is simply reflected from the surface 18 directly back to the detector 28. In FIG. 2, this component of the radiation is defined by the bundle 42 of rays. It is clear from FIG. 2 that if this were the only mode of propagation, then only an extremely small fraction of the emitted radiation would reach the detector 28. The solid angle of the detector at a distance equal to twice the length of the tube 12 is extremely small.

An important advantage of using the tube 12 is that it permits other modes of propagation from the source to the detector to occur. The amount of radiation contributed by the various modes of transmission is additive since the successive modes are characterized by progressively steeper rays. Compared with a simple plane mirror such as the surface 18, the addition of the tube 12 greatly increases the amount of radiation that reaches the detector 28. One might consider the bundle 42 of rays to represent the simplest or fundamental mode, and the ray 40 to represent one of the higher order modes of propagation.

In addition to making it possible to utilize the higher order modes of propagation, the addition of the tube 12 produces a secondary benefit, namely, that the radiation travels a greater distance through the space within the tube as the order of the mode of propagation increases. That is, for the higher modes, the rays are steeper resulting in a greater distance of travel back and forth across the tube, notwithstanding that the distance traveled in the longitudinal direction remains constant and simply equals twice the length of the tube.

In accordance with the present invention, a gas filter cell 50 is mounted within the tube 12 at any location between the detector 28 and the surface 18. In the preferred embodiment of FIG. 2, the gas filter cell is mounted within the open end of the tube 12, immediately in front of the source 26 and the detector 28, and the diameter of the gas filter cell is sufficiently large that substantially all of the radiation generated by the source 26 passes through the gas filter cell, proceeds the length of the tube 12, is reflected from the surface 18, proceeds the length of the tube 12, passes through the gas filter cell, and falls on the sensitive portion of the detector 28. Thus, the radiation passes through the gas filter cell twice-once from right to left in FIG. 2, and thereafter from left to right. A unique advantage results when a gas filter cell is mounted within the tube 12; namely, the radiation passes twice through the gas filter cell. As a result, the optical thickness of the gas filter cell is twice its actual mechanical thickness.

In the preferred embodiment, the gas sample cell includes a front window 52 and a rear window 54, both hermetically sealed to a cylindrical wall 56 that may be composed of the same material as the windows or of a different material. The material of the windows 52 and 54 is highly transmissive of radiation in the wavelength interval corresponding to the absorption band of the analyte gas. The volume of space between the windows 52 and 54 is filled with the interfering gas. This volume of interfering gas substantially absorbs the spectral components of the radiation that lie within the absorption band of the interfering gas, thereby eliminating the interference by definition. That the small volume of interfering gas can have such a strong effect is not surprising when it is remembered that in many applications the interfering gas is present in the sample chamber in relatively small concentrations, whereas in the gas sample cell the concentration of interfering gas is much greater. In those rare instances where even greater absorption by the gas filter cell is desired, the gas in the gas filter cell can be pressurized and/or the thickness of the gas filter cell can be increased. In case more than one interfering gas is present in the ambient gas, the gas filter cell can be filled with a mixture of the interfering gases. Alternatively, several gas sample cells may be used in sequence, one for each interfering gas.

The use of the gas filter cell 50 extends the performance of the gas sample chamber beyond that described in the parent application by enabling concentration measurements to be made on the analyte gas accurately and reliably, even in the presence of one or more interfering gases.

The purpose of the semipermeable membrane 22 is to prevent airborne particles larger than a predetermined size from entering the space within the tube 12, while at the same time not interfering appreciably with the free diffusion of the ambient gas into and out of the space within the tube 12. The unwanted particles include minute droplets of moisture or oil and also include fine particulate matter such as particles of dust or smoke. If these unwanted airborne particles were to enter the space within the tube 12, they would deposit themselves onto the specularly reflective surfaces thereby reducing the reflectivity and destroying its specular nature. The unwanted particles would also deposit onto the source 26 and onto the narrow passband filter 30 reducing the transmission of radiation and possibly causing chemical changes to take place. All of these problems are eliminated through the use of the semipermeable membrane which, in the preferred embodiment prevents airborne particles larger than 0.3 microns from entering the space within the tube 12.

The purpose of the semipermeable membrane 22 may be partly frustrated if the environment in which the gas sample chamber is used contains extraordinary amounts of dust or smoke particles, or of minute droplets of water or oil. During the useful life of the gas sample chamber such particles and droplets may accumulate on the semipermeable membrane to such an extent as to interfere with the desired diffusion.

In accordance with the present invention, one or more ultrasonic vibrators, of which the vibrator 60 is typical, are affixed to the tube 12. The vibrators may operate on an electromagnetic principle or they may employ piezoelectric elements. The vibrators are located adjacent the apertures 20 to minimize the power required to operate them. The vibration is transmitted through the wall of the tube 12 to the semipermeable membrane 22, causing the semipermeable membrane to vibrate. The amplitude of the vibration may be extremely small—on the order of 0.001 micron—and vibrational frequencies on the order of 100 kHz are used to avoid any conceivable interference with the data processing portion of the gas sensor.

A comprehensive theory of how the vibration of the semipermeable membrane prevents the unwanted particles from lodging on it has not yet been devised. At present the process is viewed as analogous to the condensation of water vapor onto a cold surface; the vibration being analogous to an increase in the temperature of the surface.

The semipermeable membrane cannot prevent molecules (as opposed to droplets) of water from diffusing into the space within the tube 12, and if the components within the space are at a sufficiently low temperature, there is a possibility that the water vapor may condense onto the cold surfaces. To prevent that from happening, heater wires 34 are employed in the preferred embodiment to generate heat by ohmic heating when an electric current is passed through them. To minimize the escape of this heat, the metal tube 12, which is an excellent conductor, is provided with an insulative sheath 38. Likewise, the cap 32 is provided with an insulative casing 36. Because of the proximity of the wires 34 to the source 26 and the filter 30, these components are also protected from moisture condensing upon them.

Thus, there has been described an improved diffusion-type gas sample chamber which differs from previous sample chambers in two important ways. First, one or more gas filter cells are located in the path of the radiation within the gas sample chamber to permit the concentration of an analyte gas to be measured accurately despite the presence of one or more interfering gases. Second, one or more small ultrasonic vibrators are affixed to the wall of the gas sample chamber to cause high frequency vibrations of small amplitude of the semipermeable membranes through which gases diffuse into and out of the chamber for the purpose of preventing unwanted particles from lodging on the semipermeable membrane and plugging it.

The foregoing detailed description is illustrative of one embodiment of the invention, and it is to be understood that additional embodiments thereof will be obvious to those skilled in the art. The embodiments described herein together with those additional embodiments are considered to be within the scope of the invention.

What is claimed is:

1. An improved diffusion-type gas sample chamber for transmitting radiation through gases present in the chamber by ambient pressure diffusion, the gases including an analyte gas having an absorption band and including an interfering gas having an absorption band that partially overlaps the absorption band of the analyte gas, said improved diffusion-type gas sample chamber comprising in combination:

a) an elongated hollow tube having an inner wall and having a closed end and an open end, composed of a gastight material and having a specularly-reflective surface on the inner wall and on the inwardly-facing side of the closed end;

b) said tube including a plurality of filtering apertures arrayed along said tube for improving the diffusion into and out of the space within said tube;

c) a sheet of a semipermeable membrane covering each of said plurality of filtering apertures, said semipermeable membrane permitting gases to diffuse through it under ambient pressure into and out of the space within said tube and preventing airborne particles larger than a predetermined size from entering said space;

d) a source of radiation;

e) a detector of radiation;

f) means for mounting both said source of radiation and said detector of radiation proximate said open end and facing said closed end, whereby some of the radiation emitted in various directions from said source of radiation is conducted by at least one reflection from the specularly-reflective surface on the inner wall to the specularly-reflective surface on the inwardly-facing side of the closed end and from the latter by at least one reflection from the specularly-reflective surface on the inner wall to said detector of radiation;

g) a gas filter cell located between said closed end of said tube and said detector so that radiation traveling from said source to said detector must pass twice through said gas filter cell; and, h) said gas filter cell enclosing a quantity of the interfering gas which substantially absorbs that part of the radiation generated by said source which lies in the absorption band of the interfering gas, whereby said detector receives substantially no radiation at wavelengths where the absorption band of the interfering gas overlaps the absorption band of the analyte gas, thereby rendering said improved diffusion-type gas sample chamber substantially immune to the presence of the interfering gas.

2. The improved diffusion-type gas sample chamber of claim 1 further comprising:

an ultrasonic vibrator affixed to said elongated hollow tube for imparting an ultrasonic vibration to each sheet of a semipermeable membrane to discourage the airborne particles from lodging permanently on each sheet of a semipermeable membrane.

3. The improved diffusion-type gas sample chamber of claim 1 further comprising heater means adjacent the open end of said tube for supplying heat to said tube to prevent condensation on said source of radiation, on said detector of radiation and on said specularly-reflective surface.

4. The improved diffusion-type gas sample chamber of claim 1 wherein said predetermined size is 0.3 microns.

5. The improved diffusion-type gas sample chamber of claim 1 wherein said detector of radiation further comprises a narrow passband filter.

6. An improved diffusion-type gas sample chamber for transmitting radiation through gases present in the chamber by ambient pressure diffusion, the gases including an analyte gas having an absorption band and including an interfering gas having an absorption band that partially overlaps the absorption band of the analyte gas, said improved diffusion-type gas sample chamber comprising in combination:

a) an elongated hollow tube having an inner wall and having a closed end and an open end, composed of a gastight material and having a specularly-reflective surface on the inner wall and on the inwardly-facing side of the closed end;

b) said tube including a plurality of filtering apertures arrayed along said tube for improving the diffusion into and out of the space within said tube;

c) a sheet of a semipermeable membrane covering each of said plurality of filtering apertures, said semipermeable membrane permitting gases to diffuse through it under ambient pressure into and out of the space within said tube and preventing airborne particles larger than a predetermined size from entering said space;

d) a source of radiation;

e) a detector of radiation;

f) means for mounting both said source of radiation and said detector of radiation proximate said open end and facing said closed end, whereby some of the radiation emitted in various directions from said source of radiation is conducted by at least one reflection from the specularly-reflective surface on the inner wall to the specularly-reflective surface on the inwardly-facing side of the closed end and from the latter by at least one reflection from the specularly-reflective surface on the inner wall to said detector of radiation; and, g) an ultrasonic vibrator affixed to said elongated hollow tube for imparting an ultrasonic vibration to each sheet of a semipermeable membrane to discourage the airborne particles from lodging permanently on each sheet of a semipermeable membrane.

7. The improved diffusion-type gas sample chamber of claim 6 further comprising heater means adjacent the open end of said tube for supplying heat to said tube to prevent condensation on said source of radiation, on said detector of radiation and on said specularly-reflective surface.

8. The improved diffusion-type gas sample chamber of claim 6 wherein said predetermined size is 0.3 microns.

9. The improved diffusion-type gas sample chamber of claim 6 wherein said detector of radiation further comprises a narrow passband filter.

* * * * *